United States Patent [19]
Hull

[11] Patent Number: 5,458,581
[45] Date of Patent: Oct. 17, 1995

[54] CATHETER CRIMPING APPARATUS

[76] Inventor: Michael C. Hull, 4040 Avondale, No. 301, Dallas, Tex. 75219

[21] Appl. No.: 186,813

[22] Filed: Jan. 24, 1994

Related U.S. Application Data

[63] Continuation of Ser. No. 895,549, Jun. 8, 1992, abandoned.

[51] Int. Cl.⁶ ................................................ A61M 5/00
[52] U.S. Cl. ............................ 604/248; 604/250; 251/9
[58] Field of Search ......................... 604/30, 32, 34, 604/35, 169, 181, 186, 118, 250, 275, 246, 247, 248, 902, 905, 264; 251/4, 6, 9

[56] References Cited

U.S. PATENT DOCUMENTS

| | | | |
|---|---|---|---|
| 754,000 | 8/1902 | Munro | 251/6 |
| 3,016,915 | 1/1962 | Moeller | 251/6 |
| 3,034,504 | 5/1962 | Winsor et al. | 251/9 |
| 3,191,600 | 6/1965 | Everett | 604/250 |
| 3,411,534 | 11/1968 | Rose | 604/32 |
| 3,438,607 | 4/1969 | Williams et al. | 604/902 |
| 3,554,580 | 1/1971 | Goyke | 604/283 |
| 4,061,142 | 12/1977 | Tuttle | 604/34 |
| 4,177,969 | 12/1979 | Sieber-Muller | 251/4 |
| 4,484,599 | 11/1984 | Hanover et al. | 251/4 |
| 4,524,944 | 6/1985 | Sussman | 251/4 |
| 4,662,871 | 5/1987 | Rafelson | 604/902 |
| 4,911,399 | 3/1990 | Green | 251/4 |
| 4,944,485 | 7/1990 | Daoud et al. | 251/9 |
| 4,960,259 | 10/1990 | Sunnanvader et al. | 604/250 |
| 5,000,419 | 3/1991 | Palmer et al. | 251/4 |
| 5,127,905 | 7/1992 | Lemieux | 604/264 |
| 5,224,929 | 7/1993 | Remiszewski | 604/30 |

FOREIGN PATENT DOCUMENTS 0674944  8/1990  Switzerland ............... 604/905

Primary Examiner—C. Fred Rosenbaum
Assistant Examiner—Mark Bockelman
Attorney, Agent, or Firm—Marsteller & Associates

[57] ABSTRACT

A catheter device of the type having a plastic sleeve with a central bore and a flexible catheter tube projecting from one end of the sleeve is equipped with a crimping apparatus, to allow a person administering the catheter to selectively crimp the tube to inhibit the flow of blood therethrough. The crimping apparatus includes member mounted for rotational movement with respect to the sleeve and a torsion spring, which normally biases the eccentric member to a "non-crimping" position. The member includes a bottom slot for receiving the catheter tube. When it is desired to crimp the tube, the member is rotated in a predetermined direction, such that the member compresses the catheter tube to inhibit the flow of blood therethrough. By crimping the catheter tube to inhibit the flow of blood therethrough, the likelihood of direct contact between the person administering the catheter and the catheter recipient's blood is substantially diminished.

9 Claims, 2 Drawing Sheets

CATHETER CRIMPING APPARATUS

This is a continuation of application Ser. No. 07/895,549 filed on Jun. 8, 1992 now abandoned.

FIELD OF INVENTION

This invention relates generally to catheters and in particular to a new and improved apparatus for inhibiting the flow of blood through a catheter tube.

BACKGROUND OF THE INVENTION

The current epidemic of acquired immune deficiency syndrome (AIDS) has heightened awareness of the need to protect health care professionals from contact with the bodily fluids of a person infected with AIDS. Health care professionals typically use gloves and other protective devices to prevent direct contact with the blood and other bodily fluids of a patient.

A commonly used medical procedure involves the insertion of a catheter tube into a patient's body. The catheter tube may be connected to an external tube for intravenous fluid therapy in treating patients. The catheter insertion procedure typically involves inserting a needle (i.e., stylet) through the catheter tube so that the sharp end of the stylet penetrates the patient's skin. The catheter tube is inserted through an opening in the skin made by the stylet and into the patient's vein. The stylet is then withdrawn back through the catheter tube, leaving the catheter tube in the patient's vein.

The removal of the stylet draws a small amount of the patient's blood back through the catheter tube. Therefore, blood may spurt forth from the catheter tube when the stylet is completely removed therefrom. The blood flowing through the catheter tube may come in contact with the health care professional administering the catheter, as well as other persons nearby.

There is therefore a need in the health care industry for an apparatus to inhibit the escape of blood from a catheter tube.

DISCLOSURE OF THE INVENTION

In accordance with the present invention, apparatus is provided for selectively crimping a catheter tube to inhibit the flow of blood therethrough. A typical catheter device includes an elongated sleeve and a flexible tube, a first portion of which is typically carried in the sleeve and a second portion of which projects outwardly therefrom for insertion into a person's body.

The crimping apparatus is mounted with the sleeve and includes a crimping member mounted for rotation about an axis transverse to the longitudinal axis of the sleeve without translational movement in any direction parallel to or perpendicular to the longitudinal axis. The crimping member includes an arcuate slot through which the first portion of the tube extends. The slot is defined by a generally downwardly facing convex surface.

The crimping member is rotatable by finger pressure exerted thereon between a first position at which flow through the tube is unobstructed and a second position at which the convex surface exerts sufficient pressure on the tube to obstruct flow therethrough.

In accordance with one feature of the invention, the crimping member is carried on a support shaft and is rotatable about a longitudinal axis of the shaft. A torsion spring is coupled between the support shaft and the crimping member for biasing the crimping member to the first position. The crimping member is movable to the second position by finger pressure exerted thereon sufficient to overcome the bias force.

In accordance with the present invention, apparatus is provided for substantially preventing the escape of blood from a catheter tube, such that the likelihood of direct contact between the person administering the catheter and the catheter recipient's blood is substantially diminished.

DETAILED DESCRIPTION OF THE PREFERRED EMBODIMENT

Figure 1:
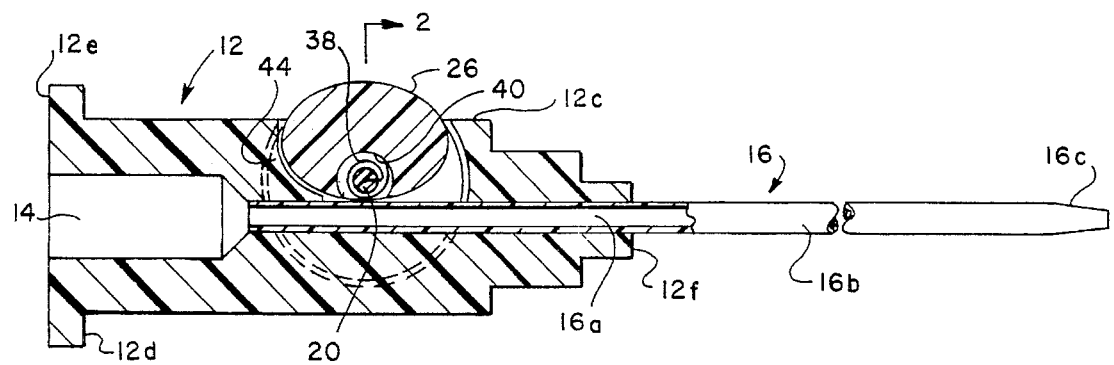
FIG. 1 is a sectional view, taken along the line 2—2 of FIG. 2, of a catheter device equipped with a crimping apparatus, according to the present invention.

In the description which follows, like parts are marked throughout the specification and drawings with the same respective reference numerals. The drawings are not necessarily to scale and in some instances proportions may have been exaggerated in order to more clearly depict certain features of the invention.

Figure 2:
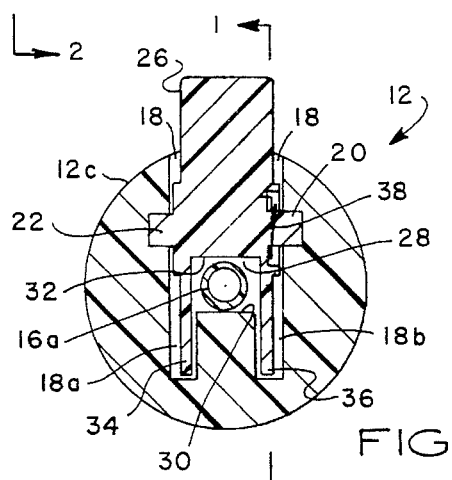
FIG. 2 is a sectional view, taken along the line 1—1 of FIG. 1, of the crimping apparatus depicted in FIG. 1.

Referring to FIGS. 1 and 2, a catheter device includes a rigid plastic sleeve 12 having substantially cylindrical first, second and third sleeve portions 12a, 12b and 12c, respectively. Sleeve portion 12b is enlarged radially with respect to sleeve portion 12a and sleeve 12c is enlarged radially with respect to sleeve portion 12b. Sleeve 12 further includes a flange portion 12d, which defines a back end of 12e of sleeve 12. Sleeve 12 includes a central bore 14, which extends longitudinally from back end 12e partially along third sleeve portion 12c. Bore 14 includes a tapered portion 14a in which the diameter of bore 14 is substantially constricted.

Catheter device 10 further includes a flexible plastic tube 16 attached to sleeve 12. A first tube portion 16a is located within sleeve 12 and is surrounded by first and second sleeve portions 12a and 12b and a part of third sleeve portion 12c forward of tapered portion 14a. A second tube portion 16b extends outwardly from sleeve 12. Second tube portion 16b extends a sufficient distance beyond front end 12f of sleeve 12 to allow a tapered end 16c of second tube portion 16b to be inserted through the skin of a catheter recipient, as will be described in greater detail.

In accordance with the present invention, a portion of sleeve 12 is hollowed out to accommodate an apparatus for selectively crimping tube 16. As can be best seen in FIG. 2, sleeve 12 includes a cavity 18 and transversely aligned recesses (not shown), which communicate with cavity 18. The recesses are adapted to receive respective stub shafts 20 and 22, such that shafts 20 and 22 are held against rotation.

A crimping member 26 is mounted on stub shafts 20 and 22 for rotation about an axis transverse to the longitudinal axis of sleeve 12. Crimping member 26 has an arcuate slot 28, which is defined by a generally downwardly facing convex surface 32. Convex surface 32 is normally in facing relationship with first tube portion 16a. First tube portion 16a extends through slot 28, as can be best seen in FIG. 2, such that first tube portion 16a is located between an upwardly facing surface 30 of third sleeve portion 12c and convex surface 32. As can be best seen in FIG. 2, convex surface 32 is recessed within slot 28. Slot 28 is bounded on either side by ears 34 and 36, which extend into respective bottom portions 18a and 18b of cavity 18.

A torsion spring 38 is in concentric relationship with stub shaft 20, as can be best seen in FIG. 2. Spring 38 is coupled between stub shaft 20 and a surface 40 of member 26. A portion of member 26 is removed to provide a recess 42 for accommodating spring 38. Spring 38 opposes the rotation of eccentric member 26 in a forward direction (i.e., clockwise, as viewed in FIG. 1). Spring 38 biases member 26 toward the position shown in FIGS. 1 and 2, which corresponds to a non-operative position of member 26, whereby first tube portion 16a is received within slot 28. Third sleeve portion 12c includes a limit member 44 to limit the rotation of member 26 in a backward direction (i.e., in a counterclockwise direction as viewed in FIG. 1).

Figure 3:
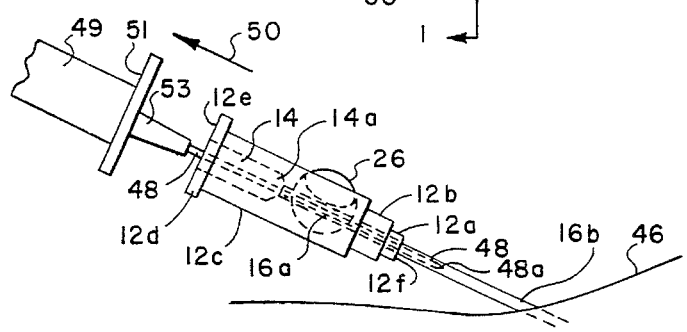
FIGS. 3–7 illustrate the sequence in which a stylet is removed from a catheter tube and a feeding tube inserted therein.

The operation of the crimping apparatus of the present invention is illustrated with reference to FIGS. 3–7. Although not shown in the drawings, tapered end 16c is inserted through an opening in a catheter recipient's skin made by the sharp tip 48a of a stylet 48. The skin surface is indicated by reference numeral 46. As shown in FIG. 3, stylet 48 is inserted through catheter tube 16. Stylet 48 is attached to a tubular handle 49 having a protective flange 51 and a tapered sleeve 53 at one end of handle 49. Stylet 48 projects from sleeve 53. After tube 16 penetrates through the recipient's skin, stylet 48 is removed by drawing stylet 48 toward back end 12e (i.e., in the direction indicated by arrow 50). When tip 48a reaches the approximate position shown in FIG. 4 (i.e., just aft of member 26, but still within tube 16), the health care professional administering the catheter manually rotates member 26 in a clockwise direction, as indicated by arrow 52, such that convex surface 32 is brought into pressure contact with tube 16, thereby compressing first tube portion 16a against surface 30, to crimp first tube portion 16a and substantially inhibit the flow of blood through tube 16.

Figure 4:
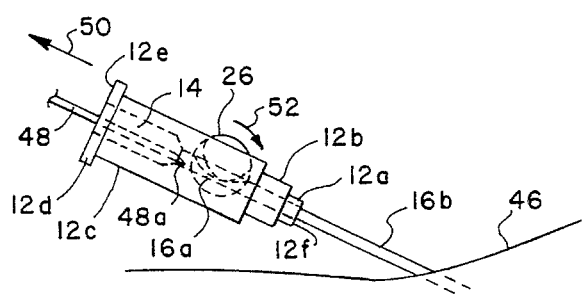

Because spring 38 opposes the clockwise rotation of member 26, the health care professional should maintain sufficient pressure on member 26 to hold it in the position shown in FIG. 4 against the spring bias. As indicated in FIGS. 3–7, a portion of member 26 protrudes outwardly from third sleeve portion 12c, to facilitate manual operation of member 26. The person administering the catheter is able to hold member 26 against the spring bias with one digit (preferably a thumb) such that the other digits can be used to grasp sleeve 12 as styler 48 is retracted from tube 16.

Figure 5:
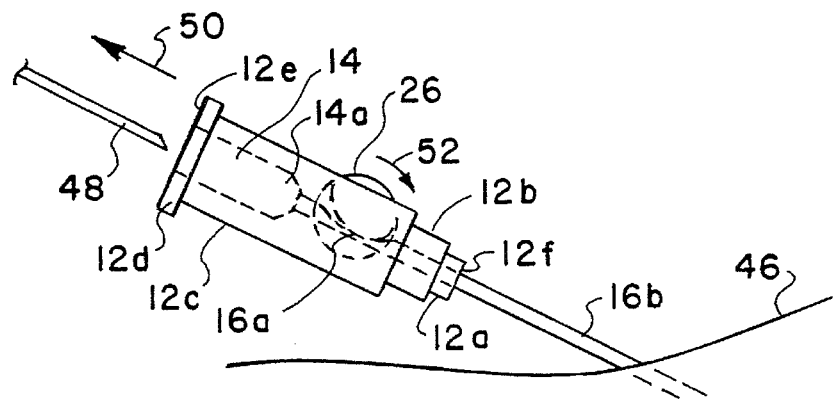
Figure 6:
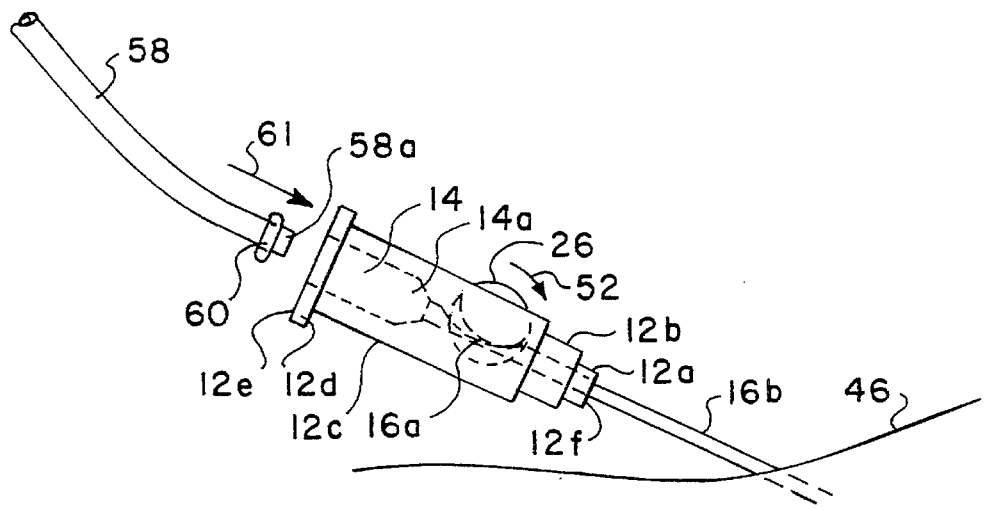
Figure 7:
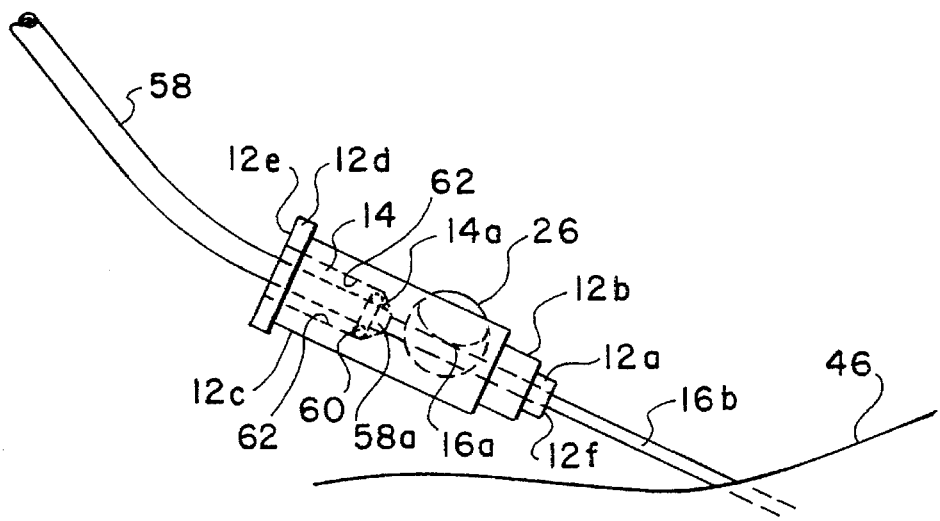

Referring now to FIGS. 5, 6 and 7, member 26 is maintained in the "crimping" position, as shown in FIGS. 5 and 6 after stylet 48 has been completely withdrawn from sleeve 12 (FIG. 5). A flexible feeding tube 58 is provided, having a flexible O-ring 60 in concentric relationship with tube 58, adjacent leading end 58a of tube 58. As can be best seen in FIG. 7, leading end 58a is inserted into bore 14, as indicated by arrow 61, until O-ring 60 encounters tapered portion 14a. O-ring 60 provides a friction seal against wall 62 surrounding tapered portion 14a, to capture any blood which may have accumulated in bore 14 within tapered portion 14a. Alternatively, bore 14 can be configured with the inner diameter of bore 14 only slightly greater than the outer diameter of tube 58, such that tube 58 fits snugly within bore 14 to prevent the backflow of any blood accumulated within bore 14.

As can be best seen in FIG. 7, after tube 58 has been fully inserted into bore 14, the person administering the catheter can now release member 26, to allow spring 38 (FIG. 1) to rotate member 26 counterclockwise back to the "noncrimping" position shown in FIG. 7.

Removal of catheter device 10 involves repeating substantially the same steps in reverse order. Before tube 58 is removed, the person administering the catheter rotates member 26 in a clockwise direction, as shown in FIG. 6, to crimp first tube portion 16a, as previously described. Tube 58 is removed from bore 14 in a direction opposite from the direction indicated by arrow 61. Tube 16 is then removed from the recipient's body according to conventional procedure. Bore 14 is preferably plugged, adjacent back end 12e, before member 26 is released, to prevent the backflow of blood through bore 14.

In accordance with the present invention, a crimping apparatus is provided to selectively inhibit the flow of blood through a catheter tube. The crimping apparatus is operable to substantially inhibit the backflow of blood through the catheter tube, particularly when the stylet is removed form the tube, thereby reducing the likelihood of direct contact between the health care professional administering the catheter and the catheter recipient's blood.

The preferred embodiment of the invention has now been described in detail. Since it is obvious that many changes in and additions to the above-described preferred embodiment may be made without departing from the nature, spirit and scope of the invention, the invention is not to be limited to the disclosed details, except as set forth in the appended claims.

What is claimed is:

1. In a catheter device of the type having a sleeve adapted for grasping by a user, a bore formed in the sleeve adapted for receiving selected devices, and a flexible tube having a passageway therethrough and in communication with the bore, a first portion of which tube is carried in and affixed to the sleeve, and a second portion of which tube projects outwardly from a front end of the sleeve and which second portion is adapted for insertion into a subject, wherein the improvement comprises:

the length of the second portion of the tube is selected such that the second portion can be inserted into the subject;

a crimping member having a first portion carried in the sleeve and a second portion protruding therefrom, whereby said crimping member is manually operable, said crimping member being selectively movable by the user when grasping the sleeve with pressure exerted by a single finger on said second portion of said crimping member between a first position at which flow through the tube is unobstructed and a second position at which sufficient pressure is exerted by the crimping member on the tube to obstruct fluid flow therethrough; and, said first portion of said crimping member having an arcuate slot for receiving the first portion of the tube, said slot being defined by a generally downwardly facing convex surface, bounded by ears said crimping member being mounted with the sleeve for rotation about an axis transverse to a longitudinal axis of the tube without translational movement of any portion of said crimping member in a direction parallel or perpendicular to the longitudinal axis.

2. The improvement of claim 1 further including a shaft member for mounting said crimping member with the sleeve, said crimping member being rotatable about a longitudinal axis of said shaft member.

3. The improvement of claim 2 further including a torsion spring coupled between said shaft member and said crimping member for biasing said crimping member to said first position, said crimping member being movable to said second position by finger pressure exerted thereon sufficient to overcome the bias force of said torsion spring.

4. In a catheter device having a sleeve adapted for grasping by a user, a bore formed in the sleeve adapted for receiving selected devices, and a flexible tube having a passageway therethrough and in communication with the bore, a first portion of which tube is carried in and is affixed to the sleeve and a second portion of which tube projects outwardly from a front end of the sleeve and which second portion is adapted for insertion into a subject, the length of the second portion of the tube is selected such that the second portion can be inserted into the subject, apparatus for selectively crimping the tube to obstruct flow therethrough, said apparatus comprising a crimping member, a first portion of which is carried in the sleeve and a second portion of which protrudes therefrom, said first portion of said crimping member having an arcuate slot for receiving the first portion of the tube, said slot being defined by a generally downwardly facing convex surface, bounded by ears said crimping member being mounted with the sleeve for rotation about an axis transverse to a longitudinal axis of the tube without translational movement of any portion of the apparatus in a direction parallel or perpendicular to the longitudinal axis, whereby said crimping member is manually operable, said crimping member being selectively movable by the user when grasping the sleeve with pressure exerted by a single finger on said second portion of said crimping member between a first position at which flow through the tube is unobstructed and a second position at which sufficient pressure is exerted by the crimping member on the tube to obstruct flow therethrough.

5. The apparatus of claim 4 further including a shaft member for mounting said crimping member with the sleeve, said crimping member being rotatable about a longitudinal axis of said shaft member.

6. The apparatus of claim 5 further including a torsion spring coupled between said shaft member and said crimping member for biasing said crimping member to said first position, said crimping member being movable to said second position by finger pressure exerted thereon sufficient to overcome the bias force of said torsion spring.

7. A catheter device, comprising:

a sleeve adapted for grasping by a user;

said sleeve is formed having a bore adapted for receiving selected devices;

a flexible tube having a passageway therethrough and in communication with said bore, and further having a first portion which is carried in and affixed to said sleeve, and a second portion projecting outwardly from a front end of said sleeve and being adapted for insertion into a subject; the length of said second portion of said tube is selected such that said second portion can be inserted into the subject;

a crimping member mounted with said sleeve for selectively crimping said tube, said crimping member having a first portion carried in said sleeve and a second portion protruding therefrom; and, said first portion of said crimping member having an arcuate slot defined by a generally downwardly facing convex surface, bounded by ears said first portion of said tube extending through said slot, said crimping member being rotatable about an axis transverse to a longitudinal axis of said tube without translational movement of any portion of said crimping member in a direction parallel or perpendicular to said longitudinal axis, whereby said crimping member is manually operable, said crimping member being selectively movable by the user when grasping the sleeve with pressure exerted by a single finger on said second portion of said crimping member between a first position at which flow through said tube is unobstructed and a second position at which sufficient pressure is exerted by the crimping member on said first portion of said tube to obstruct fluid flow therethrough.

8. The device of claim 7 further including a shaft member for mounting said crimping member with the sleeve, said crimping member being rotatable about a longitudinal axis of said shaft member.

9. The device of claim 8 further including a torsion spring coupled between said shaft member and said crimping member for biasing said crimping member to said first position, said crimping member being movable to said second position by finger pressure exerted thereon sufficient to overcome the bias force of said torsion spring.

* * * * *